(12) United States Patent
Khait et al.

(10) Patent No.: US 10,588,542 B2
(45) Date of Patent: Mar. 17, 2020

(54) SENSOR BELT CONFIGURED TO LOCALIZE AN IN-VIVO DEVICE AND METHOD FOR LOCALIZATION

(71) Applicant: GIVEN IMAGING LTD., Yoqneam (IL)

(72) Inventors: Semion Khait, Tiberias (IL); Oren Rosenberg, Kiryat Ono (IL)

(73) Assignee: GIVEN IMAGING LTD., Yoqneam (IL)

(*) Notice: Subject to any disclaimer, the term of this patent is extended or adjusted under 35 U.S.C. 154(b) by 527 days.

(21) Appl. No.: 15/324,891

(22) PCT Filed: Jul. 8, 2015

(86) PCT No.: PCT/IL2015/050711
§ 371 (c)(1),
(2) Date: Jan. 9, 2017

(87) PCT Pub. No.: WO2016/005983
PCT Pub. Date: Jan. 14, 2016

(65) Prior Publication Data
US 2017/0202479 A1 Jul. 20, 2017

Related U.S. Application Data
(60) Provisional application No. 62/022,847, filed on Jul. 10, 2014.

(51) Int. Cl.
*A61B 5/06* (2006.01)
*A61B 5/07* (2006.01)
(Continued)

(52) U.S. Cl.
CPC ............. *A61B 5/062* (2013.01); *A61B 5/073* (2013.01); *A61B 5/42* (2013.01); *A61B 5/6823* (2013.01); *A61B 5/14539* (2013.01)

(58) Field of Classification Search
CPC ......... A61B 5/062; A61B 5/6823; A61B 5/42; A61B 5/073
See application file for complete search history.

(56) References Cited

U.S. PATENT DOCUMENTS 4,278,077 A 7/1981 Mizumoto
5,383,454 A 1/1995 Bucholz
(Continued)

FOREIGN PATENT DOCUMENTS

CN 1620985 6/2005
JP 2000175863 6/2000
(Continued)

OTHER PUBLICATIONS

Office Action issued by the Japanese Patent Office for Japanese Patent Application No. 2017-500946 dated Feb. 5, 2019.

*Primary Examiner* — Nathan J Jenness
(74) *Attorney, Agent, or Firm* — Pearl Cohen Zedek Latzer Baratz LLP (57) ABSTRACT

A wearable sensor belt used as a reference frame for determining a location of an in-vivo device in the gastrointestinal (GI) tract, the belt including N magnetic field generating coils and M magnetic field sensors configured for dynamic calibration of the belt's geometry in order to accommodate for dynamic changes in the shape and/or size of the belt from one subject to another, and for dynamic changes in the shape and/or size of the belt as a result of changes in a subject's posture. A method for localizing an in-vivo device swallowed by a subject using a sensor belt is also described.

23 Claims, 7 Drawing Sheets

(51) Int. Cl.
 *A61B 5/00* (2006.01)
 *A61B 5/145* (2006.01)

(56) References Cited

U.S. PATENT DOCUMENTS

| | | |
|---|---|---|
| 5,604,531 A | 2/1997 | Iddan et al. |
| 5,662,111 A | 9/1997 | Cosman |
| 5,755,725 A | 5/1998 | Druais |
| 5,772,594 A | 6/1998 | Barrick |
| 5,993,378 A | 11/1999 | Lemelson |
| 6,161,032 A | 12/2000 | Acker |
| 6,240,312 B1 | 5/2001 | Alfano et al. |
| 6,428,469 B1 | 8/2002 | Iddan et al. |
| 6,764,440 B2 | 7/2004 | Iddan et al. |
| 6,904,308 B2 | 6/2005 | Frisch et al. |
| 6,944,316 B2 | 9/2005 | Glukhovsky et al. |
| 7,009,634 B2 | 3/2006 | Iddan et al. |
| 7,778,356 B2 | 8/2010 | Bettesh |
| 8,428,685 B2 | 4/2013 | Swain et al. |
| 9,107,604 B2 | 8/2015 | Khait et al. |
| 2002/0103417 A1 | 8/2002 | Gazdzinski |
| 2004/0068178 A1 | 4/2004 | Govari |
| 2005/0216231 A1 | 9/2005 | Aoki et al. |
| 2006/0183993 A1 | 8/2006 | Horn |
| 2007/0265496 A1 | 11/2007 | Kawano et al. |
| 2008/0193139 A1 | 8/2008 | Bettesh |
| 2008/0208077 A1 | 8/2008 | Iddan et al. |
| 2009/0131784 A1 | 5/2009 | Betesh |
| 2009/0290686 A1 | 11/2009 | Liu et al. |
| 2014/0031642 A1 | 1/2014 | Kimchy et al. |
| 2017/0000380 A1* | 1/2017 | Gotman .......... A61B 6/12 |

FOREIGN PATENT DOCUMENTS

| | | |
|---|---|---|
| JP | 2003245243 | 9/2003 |
| JP | 2005-185499 | 7/2005 |
| JP | 2006-075534 | 3/2006 |
| JP | 2009-521977 | 6/2009 |
| WO | WO 97/29685 | 8/1997 |
| WO | WO 98/35720 | 8/1998 |
| WO | 2000-506259 | 5/2000 |
| WO | WO 2007/123217 | 11/2007 |
| WO | WO 2010/006608 | 1/2010 |

* cited by examiner

SENSOR BELT CONFIGURED TO LOCALIZE AN IN-VIVO DEVICE AND METHOD FOR LOCALIZATION

CROSS-REFERENCE TO RELATED APPLICATIONS

This application is a National Phase Application of PCT International Application No. PCT/IL2015/050711, International Filing Date Jul. 8, 2015, claiming priority from U.S. Provisional Patent Application No. 62/022,847, filed Jul. 10, 2014, all of which being hereby incorporated by reference.

FIELD OF THE INVENTION

The present invention generally relates to in-vivo systems and more specifically to a wearable sensor belt that is equipped for self-calibration, and to a method for localizing an in-vivo device in a subject (for example in the gastrointestinal tract of a subject) by using the sensor belt.

BACKGROUND

In-vivo measuring systems are known in the art. Some autonomous capsule like in-vivo devices, which are swallowed and traverse the gastrointestinal (GI) system, may include an imaging sensor, or imager, for imaging (e.g., capturing images or taking pictures of) the interior of the GI system. An in-vivo device may include one or more imagers and/or one or more sensors of other types (e.g., pH sensor, pressure sensor, temperature sensor, etc.), and/or various types of tools (e.g., micro electro-mechanical system, or "MEMS"), for example to perform surgical operations in vivo and/or to administer medication in the GI system, for example from a container contained in an in-vivo device. While in operation (e.g., after swallowing), an in-vivo device may wirelessly exchange data with an external receiver. For example, the in-vivo device may wirelessly transmit data (e.g., sensory data; e.g., image data pertaining to captured images) to the external receiver, and the external receiver may wirelessly transmit instructions back to the in-vivo device, for example instructions that may depend on data transmitted from the in-vivo device. For example, the in-vivo device may transmit image frames to the receiver, and the receiver may transmit an instruction to the in-vivo device, for example, to change the image frame capturing rate, for example, based on captured images. (An image frame is a data block/set that may include image data (and/or other sensory data), metadata, synchronization data, etc.)

In many cases, it may be important to associate a captured image or a sensor's measurement with the location in the GI tract at which the image (or measurement) was taken, or a physiological parameter (e.g., pH, pressure, etc.) was sensed in order to interpret the image or measurement properly. For example, a pH value equal to, say, 6.3 may be regarded as normal if it is measured in one GI portion and abnormal if it is measured in another portion of the GI tract.

Magnetic based localization systems enable localization of in-vivo devices in the GI tract. Typically, a magnetic localization system is external to the subject, stationary and robust. A magnetic based localization system typically includes one or more magnetic field sources to generate magnetic fields in order for them to be sensed in/by the in-vivo device whose location is sought. Since conventional localization systems are stationary, freedom of movement of the subject swallowing the in-vivo device is very limited.

SUMMARY

While using a magnetic localization system to localize an in-vivo in the GI tract is beneficial in general, it would be beneficial to have a magnetic localization system that is wearable and, yet, enables accurate localization of an in-vivo device.

A wearable sensor belt for localizing an in-vivo device may include an electrical circuit comprising a number N (N being an integer) of magnetic coils for generating magnetic field(s), for example by using one magnetic coil at a time, and a number M (M being an integer) of magnetic field sensors for sensing the magnetic field(s). The wearable sensor belt's electrical circuit may include a magnetic coils switching module to enable; e.g., in-situ or remote controller to selectively activate (generate magnetic field by) magnetic coils ('coils'), and a magnetic field sensors switching module to enable, for example the controller, to select sensors for sensing magnetic field(s). The magnetic coils and the magnetic field sensors may be distributed equidistantly, or otherwise, in or on the sensor belt, for example along the length of the sensor belt. The N magnetic coils may be interspersed between or among the M magnetic field sensors.

The magnetic coils switching module may be connected to the N magnetic coils via a first bus ('first coils bus'), and to an external system (which may be or include a data recorder) via a second bus ('second coils bus').

The magnetic sensors switching module may be connected to the M magnetic field sensors via a first bus ('first sensors bus'), and to the external system via a second bus ('second sensors bus').

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

The description that follows provides various details of exemplary embodiments. However, this description is not intended to limit the scope of the claims but instead to explain various principles of the invention and the manner of practicing it.

Unless explicitly stated, the embodiments of methods described herein are not constrained to a particular order or sequence of steps, operations or procedures. Additionally, some of the described method embodiments, steps or elements thereof can occur or be performed simultaneously or concurrently.

Figure 1:
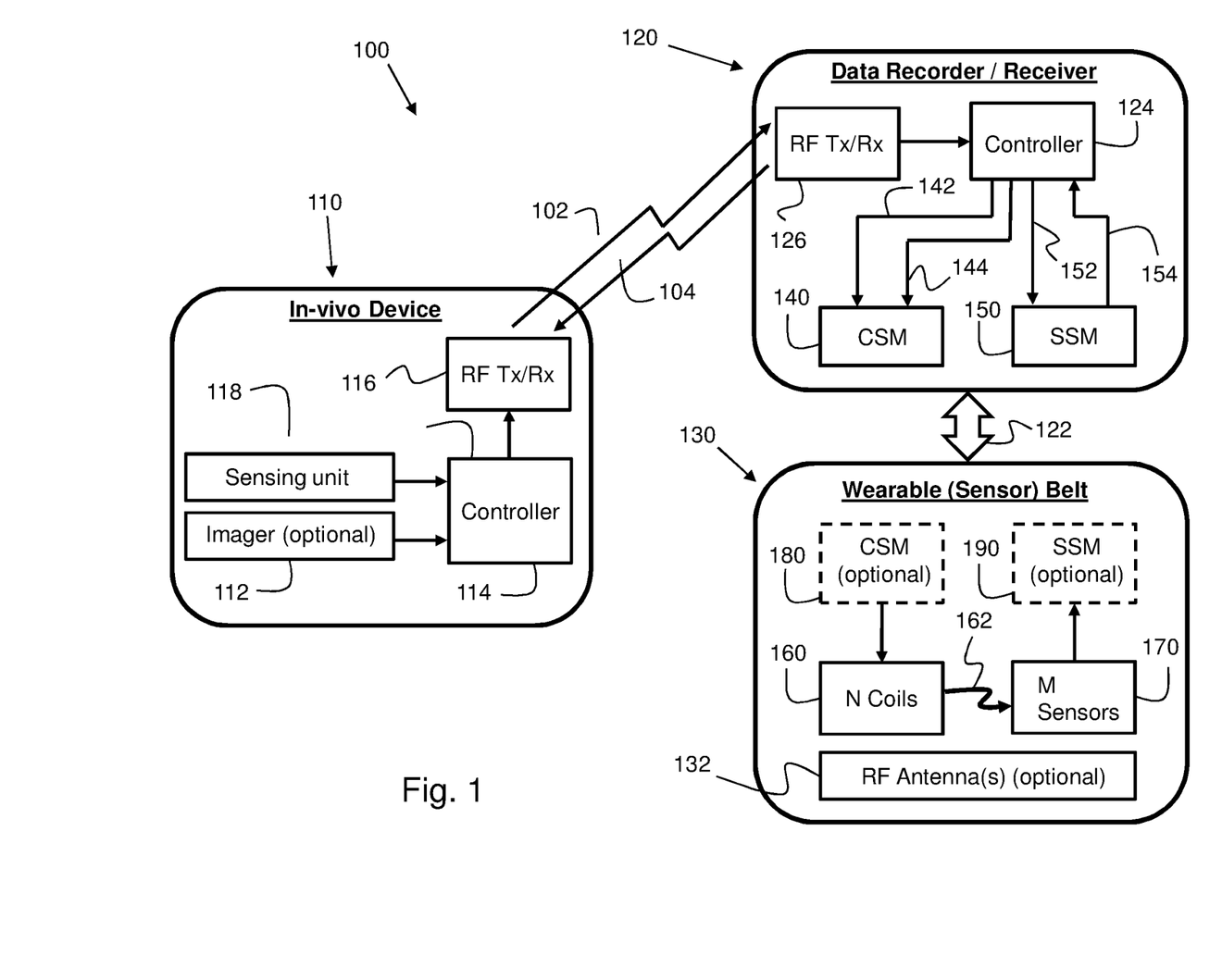
FIG. 1 shows a block diagram of an in-vivo device localization system according to an example embodiment of the present invention.

FIG. 1 shows a block diagram of an in-vivo system 100 according to an example embodiment of the present invention. In-vivo system 100 may include an in-vivo device 110, a data recorder 120 and a sensor belt, garment, or vest 130. In-vivo device 110 may include an imager 112 for taking images inside a subject body, for example inside the GI tract (and/or additional or other sensor(s) for sensing a parameter of the GI tract), a controller 114 for transmitting images (and/or the other sensory data) to data recorder 120 by using a radio frequency ("RF") transceiver 116, and a sensing unit 118 for sensing magnetic fields generated, for example, by sensor belt 130 during a localization procedure. Sensing unit 118 may include a three-dimensional (3-D) magnetic sensor (e.g., 3-D magnetometer) for sensing magnetic fields in three, for example orthogonal, axes.

Data recorder 120 may include a RF transceiver 126 for exchanging data with (for example receiving data from, and, optionally, transmitting data to) RF transceiver 116, and a controller 124 for managing the data received (102) from in-vivo device 110 and, optionally, data or control messages (e.g., instructions) that have to be sent (104) to in-vivo device 110, for example in order to change an operation mode of in-vivo device 110. RF transceiver 116 may transmit various types of data (e.g., sensory data; e.g., image data, localization data, etc.) to data recorder 120 via uplink communication channel 102, and receive various types of data/information, messages and/or instructions from data recorder 120 via downlink channel 104.

Controller 124 may be a processor or controller, for example, a central processing unit processor (CPU), a chip or any suitable computing or computational device. Controller 124 may be configured to carry out all or part of a method according to the present invention by for example executing software or code.

Data recorder 120 may include RF antennas (which are not shown in FIG. 1) to facilitate communication with RF transceiver 116 of in-vivo device 110. Alternatively, such antennas may be embedded or included in sensor belt, garment, or vest 130, as shown at 132.

Data recorder 120 may also include a coils switching module ("CSM") 140 to facilitate controlled (e.g., timely, selective) activation of N magnetic coils, and a sensors switching module ("SSM") 150 to facilitate controlled (e.g., timely, selective) reading of M magnetic coils. Controller 124 may be connected to CSM 140 by/via a coils control bus 142 via which controller 124 may send control data to CSM 140, for example, to select or determine the coils to be activated. Controller 124 may also be connected to CSM 140 by/via a coil signal bus 144 via which controller 124 may send electrical currents to selected coil(s) to thereby generate magnetic field(s). A magnetic field generated by any of the N coils may be sensed by one or more of the M (magnetic) sensors. Controller 124 may be connected to SSM 150 by/via a coils control bus 152 via which controller 124 may send control data to SSM 150, for example, to select sensor outputs for (measurement) reading (and also to read, process and interpret the selected sensor outputs). Controller 124 may also be connected to SSM 150 by/via a sensors data bus 154 via which controller 124 may receive data representing magnetic field(s) as sensed by any sensor or selected sensors of the M sensors. The N magnetic coils may be interspersed between, e.g., distributed among, the M magnetic field sensors, for example such that for some coils the coils are next to sensors rather than being all grouped together.

Wearable belt 130 may include N coils (160) for generating magnetic field(s), for example, by being selectively activated (e.g., individual or a subset of coils may be activated) by controller 124. Controller 124, by using CSM 140, may generate a magnetic field by using one of coils 160 at a time, or any number of coils at a time, for example 2 coils at a time or, first, one coil at a time and then a greater number of coils at a time, etc. Wearable belt 130 may also include M magnetic sensors (170) for sensing (162) the magnetic field generated by any one of magnetic coils 160. A measurement value, or values, corresponding to or representing, for example, the magnitude (and, optionally, the direction) of the sensed magnetic field(s) may be read, for example, by controller 124, for example by using, or via, SSM 150.

Wearable belt, garment or vest 130 may optionally include a CSM 180 similar to CSM 140, via which controller 124 may select or determine magnetic coil(s) for activation. Wearable belt 130 may optionally include a SSM 190 similar to SSM 150 via which controller 124 may select sensors for reading sensed magnetic fields. System 100 may include only CSM 140 and SSM 150, or only CSM 180 and SSM 190, or CSM 140 and SSM 150 and CSM 180 and SSM 190, or CSM 140 and SSM 150 and any of CSM 180 and SSM 190, or CSM 180 and SSM 190 and any of CSM 140 and SSM 150. Data recorder 120 may communicate with wearable belt 130, via a communication channel 122, the control data/signals by which controller 124 may select and activate magnetic coils 160 in order to generate magnetic field(s), and also control data/signals by which controller 124 may select sensors (170) and read sensor outputs in order to measure the magnetic field as sensed by one or more of sensors 170.

Magnetic coils 160 may be used in two modes of operations: (1) localization, and (2) sensor belt calibration. In the first operation mode (localization mode) coils 160 may be activated (e.g., by controller 124 or by a controller embedded or included in belt 130) to generate a magnetic field(s) that may be sensed in/by in-vivo device 110, for example by sensing unit 118. (Sensing unit 118 may include one or more 3-D magnetometers. Briefly, a magnetometer is a device designed to measure the strength and the direction of a magnetic field at a point in space.) Generating magnetic fields by magnetic field sources that are embedded or included in a wearable belt and sensing these magnetic fields by sensor coils that are also embedded or included in the sensor belt facilitates or enables (e.g., by using triangulation) determination of a spatial location, for example, of in-vivo device 110 in the GI tract. (The in-vivo device whose location is sought may be in the plane of the wearable belt or in a different plane, and using magnetic fields with a priori known characteristics enables determining the distance between the in-vivo device and the (selected) magnetic coils.) A controller embedded or included in sensor belt 130 may selectively activate the magnetic coils embedded or included in the belt to generate magnetic field(s), and it may selectively use magnetic field sensors, which are also embedded or included in the belt, to sense the magnetic field(s). The controller embedded or included in sensor belt 130 may replace controller 124 in generating and sensing the magnetic field(s), that is, in performing the belt calibration procedure. The controller embedded or included in sensor belt 130 may cooperate with controller 124 in generating and sensing the magnetic field(s).

Localizing or determining a location of a device (e.g., in-vivo device 110) requires a reference frame that defines a coordinate system. The wearable belt or the sensors on the belt may be used as a reference frame against which the location of in-vivo device 110 may be measured. However, the size and shape of a belt (e.g., rounded, ring-shaped, egg-shaped, oval-shaped, etc.) may change according to (to suit) the body shape or body mass index ("BMI") of the subject wearing it. That is, some subjects are slim, some are fat, and many are between these two extremes. The shape of the belt may also change as a result of a subject movement (e.g., when the subjects walk or changes postures). Assuming magnetic coils 160 and magnetic sensors 170 are mounted in/on wearable belt 130 in a certain way, for example the N coils (160) and the M sensors (170) may be equidistantly spaced on the belt (when the belt aligns with, or forms, a straight line), the distances between coils of magnetic coils 160 and sensors of magnetic sensors 170 (and also between magnetic coils and/or between magnetic sensors) may change, when the belt is worn, according, for example, to the subject body size and/or shape. This may change the accuracy of the localization process, which calls for a dynamic calibration of the distances between the belt's magnetic coils and the belt's magnetic sensors, hence the second operation mode (belt calibration). The term "belt calibration", as used herein, refers to a process by which the size and shape of a worn belt (e.g., rounded, ring-shaped, egg-shaped, oval-shaped, etc.) and/or the position of sensors and/or coils on the belt is determined based on magnetic fields that the belt's magnetic coils generate and the belt's magnetic field sensors sense.

While magnetic coils 160 may be used in localization and calibration processes, magnetic field sensors 170 may be used only, or primarily, for belt calibration. The belt calibration process is more fully described in connection with, for example, FIG. 2, which is described below.

Figure 2:
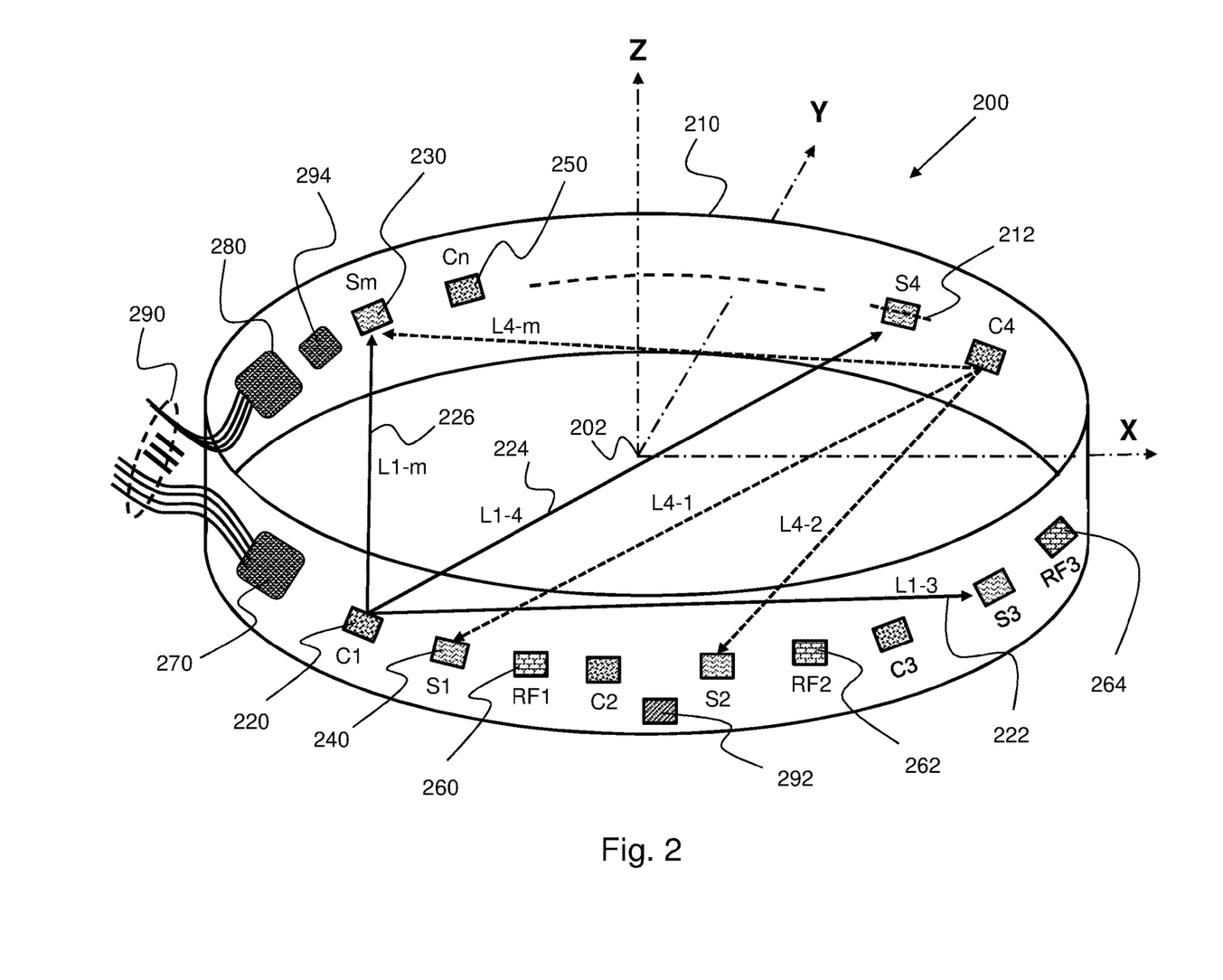
FIG. 2 shows a sensor belt according to an example embodiment of the invention.

FIG. 2 shows a wearable sensor belt 200 system according to an example embodiment. Sensor belt system 200 may include a belt 210, N on-board magnetic coils (which are designated as coils C1 (C1 is shown at 220), C2, . . . , Cn (Cn is shown at 250)) for generating magnetic fields, and M on-board magnetic field sensors (which are designated as sensors S1 (S1 is shown at 240), S2, . . . , Sm (Sm is shown at 230)) for sensing magnetic fields, for example the magnetic fields generated by any of the N magnetic coils, and extraneous magnetic fields that may be or include interference magnetic fields that may be generated by magnetic field sources other than magnetic coils C1-Cn. The N magnetic coils and the M magnetic field sensors may be distributed in/on sensor belt 200 equidistantly along the length of the sensor belt, though they may be distributed along the length of sensor belt 200 in other ways. In one embodiment, belt or garment 200 (and other belts, garments or vests disclosed herein) may have a length and a width, and the coils and sensors may be distributed along the length in the sense that the coils and sensors may lengthwise be distributed generally along an axis corresponding to the length of the belt or garment. Other distributions may be used.

Wearable sensor belt 200 system may also include on-board radio frequency ("RF") antennas via which a receiver similar to receiver 120 of FIG. 1 may exchange data and/or instructions/commands with an in-vivo device similar to in-vivo device 110 of FIG. 1. By way of example, wearable sensor belt 200 system is shown including three on-board RF antennas, which are designated as RF1 (antenna RF1 is shown at 260), RF2 (shown at 262) and RF3 (shown at 264). Other numbers of RF antennas may be used.

Wearable sensor belt 200 system may also include an on-board coils switching module (CSM) 270, which may be similar to, and function like, for example, CSM 180 of FIG. 1, and an on-board sensors switching module (SSM) 280, which may be similar to, and function like, for example, SSM 190 of FIG. 1. CSM 270 and SSM 280 may electrically be wired to a receiver via an electrical buss 290, and the receiver may be similar to receiver/data recorder 210 of FIG. 1.

Each of magnetic sensors S1 through Sm, or magnetic sensors selected from magnetic sensors S1-Sm, may include one or more (e.g., three) magnetometers, or magnetic sensors of other types. For example, a sensor, or sensors, of sensors S1-Sm may include a set of magnetometers to sense a magnetic field in each coordinate of a predefined coordinate system. For example, in a Cartesian coordinate system a first magnetometer, Mx, of sensor Si (i=1, 2, . . . , m) may be configured to sense magnetic field in the 'X' direction, a second magnetometer, My, of the sensor may be configured to sense magnetic field in the 'Y' direction and a third magnetometer, Mz, of sensor Si may be configured to sense magnetic field in the 'Z' direction.

Belt 210 may define, and be used as, an X-Y-Z coordinate system. The X-Y-Z coordinate system defined by belt 210 may be used as a reference frame for detecting a spatial location of an in-vivo device (e.g., in-vivo device 110 of FIG. 1). A plane on which (buckled) belt system 210 lies may define an X-Y plane, with the Z axis being perpendicular to the X-Y plane (to the belt plane), as shown in FIG. 2. The origin point (202) of the Cartesian coordinate system may lie on the X-Y plane and coincide with a geometrically defined reference point of, or associated with, or derived from belt 210. The geometrically defined reference point of, associated with or derived from belt 210 may be a center point of belt 210 on the X-Y plane, and may be defined or determined in various ways, for example it may be determined geometrically, be defined as a 'center of mass' of belt 210, etc. Any of magnetic oils C1 through Cn (or any of magnetic field sensors S1 through Sm) may be used as a reference point (e.g., origin point) for a coordinate system that is used to locate an in-vivo device. For example, coil C1 may be used as a reference point, or as an origin, of a reference frame or coordinate system, and the location of each other coil and the sensors may be determined relative to the location of coil C1.

In order to determine the location of the origin point of the Cartesian coordinate system, the geometrical characteristics (e.g., geometric shape, Sh, and size, Sz) of belt, vest or garment 210 may be determined (e.g., calculated) magnetically, by generating magnetic fields by magnetic coils selected from coils C1-Cn, by using one coil at a time and simultaneously/concurrently sensing, by sensors of sensors S1-Sm, the magnetic field generated by each magnetic coil. In one embodiment, it is the positional arrangement of the coils and/or sensors in or on the belt or garment that is calculated or determined, and from this the geometry or shape of the belt or garment may be determined.

The magnitude of the magnetic field and the direction of the magnetic gradients generated by each magnetic coil may be known in advance, for example to a controller (e.g., controller 124 of FIG. 1), for example by using a stored magnetic field map or magnetic field look-up table that was prepared in advance. In addition, the controller may also 'know', in advance, the orientation of each magnetic sensor, Si, relative to the belt portion/segment it is mounted on/in.

That is, the spatial orientation of a portion or segment of the sensor belt may be equal to, or otherwise be derived from, and therefore represented by, the spatial orientation of the pertinent magnetic sensor. For example, the spatial orientation of a portion or segment 212 of sensor belt 210 may be equal to, or otherwise be derived from, and therefore represented by, the spatial orientation of magnetic sensor S4. Therefore, a distance, Li-k, between a magnetic sensor Si and a magnetic coil Ck generating a magnetic field may be calculated based on measured magnetic magnitude, and the spatial orientation of segments of belt 210 may be calculated based on the direction(s) of the magnetic field sensed by the magnetic sensors that were selected by the controller.

By way of example, controller 124 of FIG. 1, or a similar controller, may first activate, for example, only coil C1 to generate a magnetic field whose magnetic characteristics (e.g., magnitude, direction, gradient, etc.) are known in advance, and simultaneously measure only signals that are output, from example, from/by magnetic sensors S3, S4 and Sm. The controller may calculate the distance L1-3 (shown at 222) between coil C1 and sensor S3 based on the signal(s) that sensor S3 outputs; the distance L1-4 (shown at 224) between coil C1 and sensor S4 based on the signal(s) that sensor S4 outputs, and the distance L1-m (shown at 226) between coil C1 and sensor Sm based on the signal(s) that sensor Sm outputs. Then, the controller may activate, for example, only coil C4 to generate a magnetic field (whose magnetic characteristics are known in advance) and simultaneously measure only signals that are output, for example, from/by magnetic sensors S1, S2 and Sm. The controller may calculate: (1) the distance L4-1 between coil C4 and sensor S1 based on the signal(s) that sensor S1 outputs; (2) the distance L4-2 between coil C4 and sensor S2 based on the signal(s) that sensor S2 outputs, and (3) the distance L4-m between coil C4 and sensor Sm based on the signal(s) that sensor Sm outputs. The controller may select any magnetic coil Ci to generate a magnetic field and simultaneously select any magnetic sensor to sense a magnetic field which is generated by a particular magnetic coil Ci. Continuing the example above, the controller may also calculate the orientations of sensors S3, S4, Sm based on the magnetic field generated by coil C1, and the orientations of sensors S1, S2, Sm based on the magnetic field generated by coil C4. The magnitudes of the magnetic fields generated by coils C1 and C4, as measured by sensors S1, S2, S3 and Sm (per the example above) may enable the controller to calculate the size and shape (e.g., curvature) of belt 210. The controller may use the belt's size and shape information as calibration information, or to calibrate belt 210 as a reference frame. The controller may determine/calculate the center point of the belt, and it may determine that the determined/calculated center point of the belt is an origin point of a coordinate system (e.g., Cartesian coordinate system) relative to which a 3-D location of an in-vivo device (e.g., in-vivo device 110) may be determined. Any number of magnetic coils and magnetic field sensors may be used to determine the geometric shape and size of belt 210.

Example Table-1 (the table is shown below) facilitates calibration of sensor belt system 200. Coils C1 through Cn and sensors Si through Sm are distributed along the length of sensor belt 210. The values V1-1 through Vn-m in Table-1 may be obtained as described above. For example, a controller may cause, for example, only coil C1 to generate a magnetic field of known magnetic parameters, and, while C1 is activated, it may simultaneously sense the magnetic field using all sensors (S1-Sm) or selected sensors, for example sensors S1, S2 and Sm. The values sensed by the selected sensors (in this example sensors S1, S2 and Sm) as a result of the activation of coil C1 are respectively shown, in Table-1, as values V1-1, V1-2 and V1-m. To continue the example, the controller may then deactivate coil C1 and activate, for example, only coil C2 to generate a magnetic field of known magnetic parameters, and, while C2 is activated, it may simultaneously sense the magnetic field using all sensors (S1-Sm) or selected sensors, for example sensors S1 and Sm. The values sensed by sensors S1 and Sm as a result of the activation of coil C2 are respectively shown, in Table-1, as values V2-1 and V2-m. Other or additional coils may be activated in a similar way, and any sensors (including any number and in any location on belt 210) may be used to sense the magnetic field generated by each used/selected coil.

Each table value, Vi-k (i=1, 2, . . . , n; k=1, 2, . . . , m), may be converted to a corresponding distance, Li-k. For example, based on the known magnetic characteristics of the magnetic field generated by coil C1 and the measured value V1-1, the distance between coils 1 and sensor, L1-1, may be determined/calculated. Distances between other selected coils and selected sensors may be determined in the same way as the distance L1-1. The coil-sensor distances information of Table-1 enables the controller to characterize belt 210 geometrically, for example to determine the belt's shape and size.

TABLE 1

|  | Sensor S1 | Sensor S2 | - - - | Sensor Sm |
|---|---|---|---|---|
| Coil C1 | V1-1 (L1-1) | V1-2 (L1-2) | - - - | V1-m (L1-M) |
| Coil C2 | V2-1 (L2-1) | N/A | - - - | V2-m |
| Coil C3 | N/A | V3-2 (L3-2) | - - - | N/A |
| - - - | - - - | - - - | - - - | - - - |
| - - - | - - - | - - - | - - - | - - - |
| Coil Cn | Vn-1 (Ln-1) | Vn-2 (Ln-2) | - - - | Vn-m (Ln-m) |

The calibration content/information of Table-1 may be updated according to a need to know the location of an in-vivo device. For example, if it is desired to know the location of the in-vivo device once every hour, the content of Table-1 may be updated accordingly, that is once every hour, preferably a short while before each localization process is started. The calibration content/information of Table-1 may be updated, and a belt geometry calculation using the information of Table-1 may be performed, occasionally or intermittently, for example once every time period or periodically (e.g., once every 50 milliseconds), once every a predetermined number of image frames (e.g., before, during or after each frame, once every 5 frames, etc.) or according to other predetermined criteria or changed criteria, during the time the sensor belt is worn by a subject, to determine the belt's dynamically changing geometry (to accommodate for changes in the belt's geometry while the subject wearing the belt is, for example, changing posture or is moving). A rate at which the information of Table-1 may be updated may depend, for example, on movements of the subject. For example, the faster the subject moves, the more frequently the table's information may be updated, assuming, for example, that the location of the in-vivo device has to be determined that frequently. A movement sensor 292 embedded or included in sensor belt 210 may provide the movement information. Movement sensor 292 may include, for example, an accelerometer. Knowing the belt's current shape or geometry means 'knowing' (e.g., by a controller) the relative location of at least some of the coils and/or sensors from the magnetic field information measured by selected magnetic sensors. In cases where only some of the coils and/or some of the sensors are used in the belt's geometry determination process or calculation, the location of other sensors and/or coils on the belt may be interpolated using location information of used sensors and/or used coils. The sensor belt geometry calculation/determination may be performed according to a criteria. A criterion may be selected based on, or using, past (e.g., known) geometries of the belt. That is, past known sensor belt's geometries may be used to estimate or calculate next sensor belt's geometries.

Any magnetic coil or magnetic field sensor on sensor belt 210 may be used as a reference point, or origin point, for determining the coordinates of the other coils and/or sensors. That is, the location of sensor S1 (shown at 240) may be S1{x1;y1}, the location of sensor S2 may be S2{x2;y2}, the location of sensor S3 may be S3{x3;y3}, and so on, where coordinates {x1;y1}, {x2;y2}, {x3;y3,} and so on, may be calculated relative to the location of a particular coil Ci, which may be designated as 'Ci{x0,y0}'. For example, coil C1 (shown at 220) may be used as a reference point, or origin point, and the location (e.g., in X-Y coordinates) of each sensor and/or coil may be determined with reference to the location of coil C1.

Some coils on a belt may be used to determine the location of sensors on the belt, and knowing the location of the sensors may be used to determine the location of other coils. For example, a location of a coil may be determined from known locations of sensors by activating the coil (causing it to generate a magnetic field with known magnetic characteristics), sensing the magnetic field generated by the coil by several sensors whose location is already known, and calculating the location of the coil using the magnetic field as sensed by the sensors.

A controller 294 embedded or included in belt or garment 210 may selectively activate the magnetic coils embedded or included in belt or garment 210 to generate magnetic field (s), and it may also selectively use magnetic field sensors, which are also embedded or included in the belt, to sense the magnetic field(s). Controller 294 may replace controller 124 of FIG. 1 in generating and sensing the magnetic field(s), that is, in performing the belt calibration procedure. Controller 294 may cooperate with controller 124 to generate and sense the magnetic field(s).

Figure 3A:
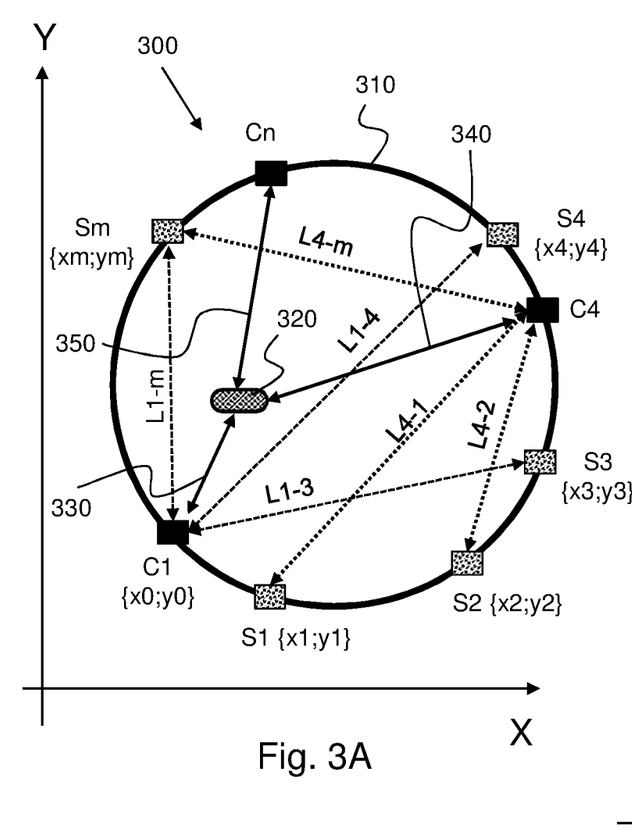
FIGS. 3A-3C illustrate comparative shapes of the sensor belt of FIG. 2.
Figure 3B:
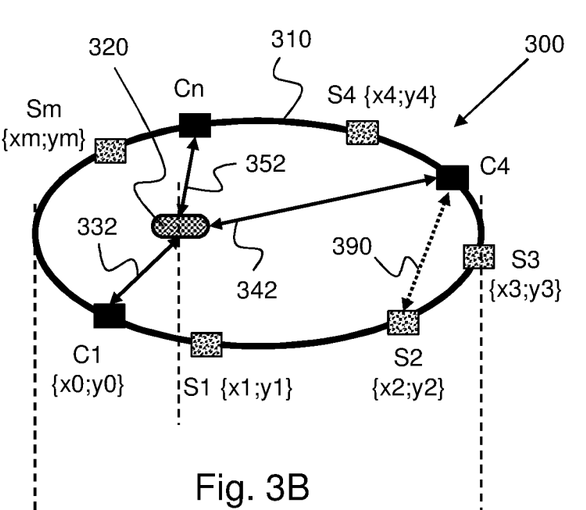

FIGS. 3A-3B show a sensor belt 300 system similar to sensor belt system 200 in two positions in accordance with an example embodiment of the present invention. As the body size and shape of a subject may change, so does the size and shape of the belt worn by the subject. When a relatively fat and rounded subject wears a sensor belt 310, sensor belt 310 may look more like the belt shown in FIG. 3A. When a relatively slim and 'flat' subject wears sensor belt 310, sensor belt 310 may look more like the belt shown in FIG. 3B.

Referring to FIG. 3A, magnetic coils and magnetic sensors may be used, as described herein, to calibrate sensor belt 310 to (to determine or calculate the belt's current geometry or shape, or the positional arrangement of the coils and/or sensors in or on the belt or garment) the particular subject who wears it, which, in this example, is relatively fat and rounded. During the calibration process the distances between coils and sensors (e.g., L1-3, L1-4, L1-M, L4-1, L4-2 and L4-M) may be determined as described herein.

The calibration process may result in (it may provide) the magnetic characteristics (e.g., magnitude, magnetic gradient) that each coil participating in the localization process should have. For example, the larger the belt, the stronger the magnetic field that each coil, or selected coils, should generate. In other words, the controller may adjust the magnetic fields generated by the coils based on, or in accordance with changes in the belt's geometry. Alternatively, the magnetic fields generated by the coils may each time have the same magnetic values, and the controller may compensate for, or adjust the, the localization readings (e.g., the magnetic measurements measured by (e.g., inside) the in-vivo device whose location is to be detected by the controller.

After a calibration procedure is completed, the current geometry or shape of sensor belt 310 may be determined/ calculated, and a location of an in-vivo device (e.g., in-vivo imaging device), or capsule (shown at 320), in the subject wearing the belt may be calculated based on the belt's determined/calculated geometry and relative to the reference frame formed, embodied or represented by the belt's geometry or relative to a coordinate system, for example a coordinate system defined by or whose location is determined relative to the belt.

During a localization process, the controller may activate only a first coil (say coil C1) and wirelessly receive, as feedback, localization data from capsule 320 that represents the magnitude of the magnetic field as sensed by (e.g., inside) capsule 320. (The capsule may also sense and send orientation of the capsule relative to the direction of the magnetic field it senses.) This information may enable the controller to calculate, for example, a distance (330) between coil C1 and capsule 320 (and optionally the capsule's orientation). The controller may then deactivate coil C1 and activate a second coil (say coil C4) and receive localization data from capsule 320 to calculate a distance (340) between coil C4 and capsule 320. The controller may then deactivate coil C4 and activate a third coil (say coil Cn) and receive localization data from capsule 320 to calculate a distance (350) between coil Cn and capsule 320. Then, the location of capsule 320 may be determined using triangulation, with distances 330, 340 and 350 being used in the triangulation process.

Figure 3C:
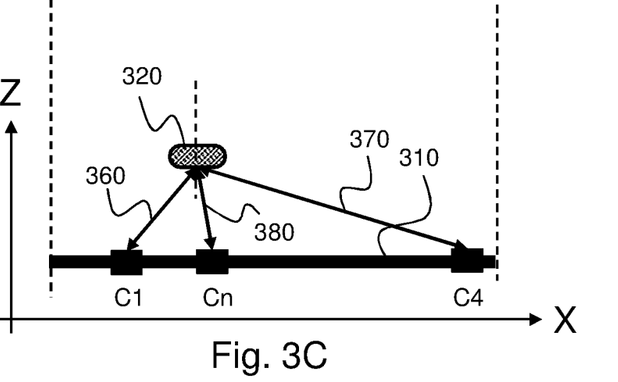

When belt 310 is adjusted to a relatively slim person, all or some of the distances between coils and sensors and/or between coils and other coils may change, as demonstrated by FIG. 3B. For example, in FIG. 3A, the distance between coil C4 and sensor S2 (distance L4-2 in FIG. 3A) is greater than distance 390 (see FIG. 3B) between the same two devices after belt 310 is 'flattened'. Continuing the comparison between FIG. 3A and FIG. 3B, the result of the flattening of belt 310 is, for example, a shorter distance 342 (FIG. 3B) between capsule 320 and coil C4, comparing to distance 340, and a shorter distance 352 (FIG. 3B) between capsule 320 and coil Cn, comparing to distance 350. However, since the belt's geometry is continually monitored, changes in coil-sensor distances are detected and accommodated for by the controller. That is, the controller may initiate the calibration process described herein in order to detect, in real time, any change that may occur in the geometry of the belt. Detecting changes in the belt's geometry means that, or enables the controller to, (re)adjust the reference coordinate system represented or formed by some or all the coils and/or by some or all the sensors. FIG. 3C shows belt 310 of FIG. 3B in profile. The location of capsule 320 may be triangulated using, for example, calculated distances 360, 370 and 380 in a similar way as described herein.

Figure 4:
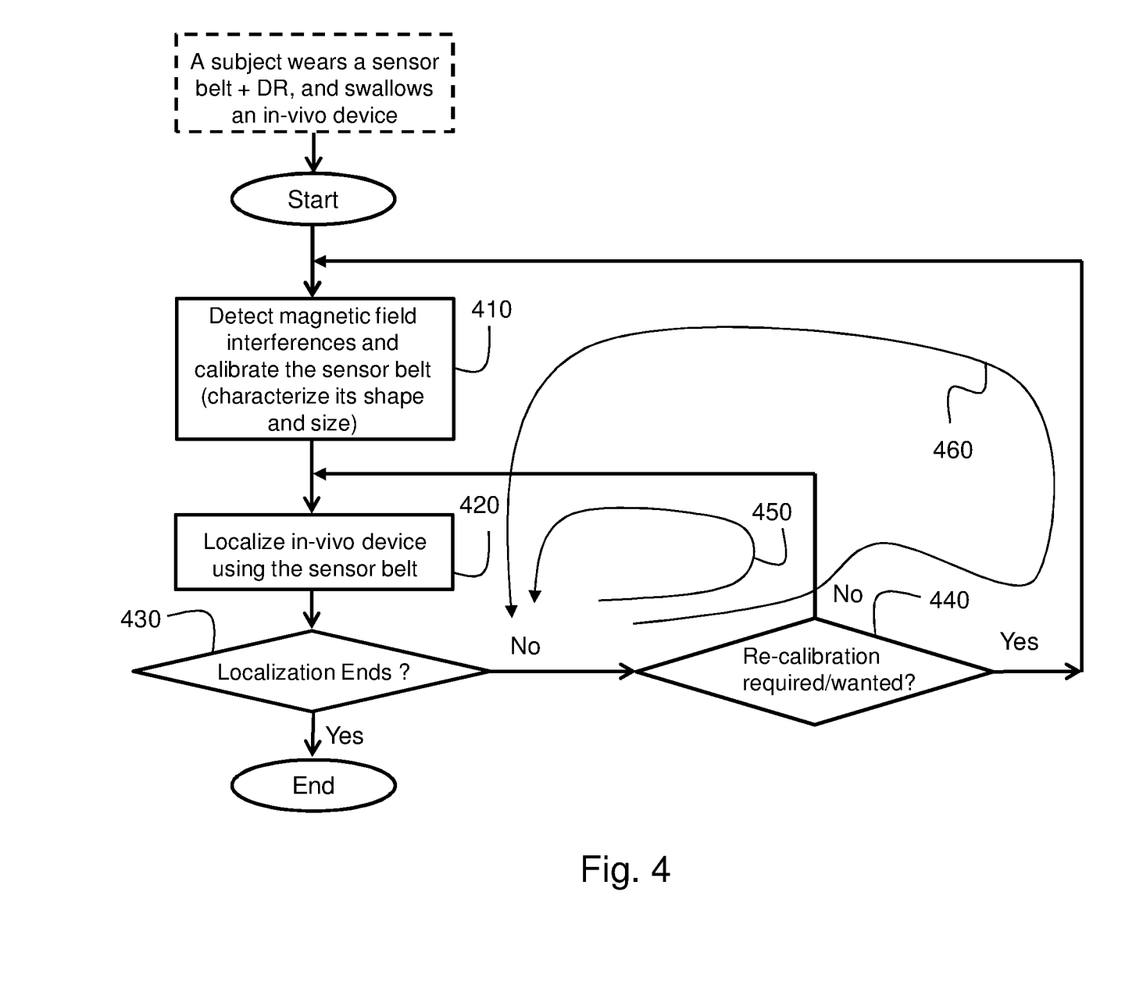
FIG. 4 shows a method for localizing an in-vivo device according to an example embodiment of the invention.

FIG. 4 shows a method for operating/using belt 200 and belt 310 according to an example embodiment of the invention. Steps described in connection with the method shown in FIG. 4, and with the other methods disclosed herein, may be performed by a controller, for example by controller 124 of FIG. 1 or by a similar controller. Assume that a subject wears a sensor belt, garment, or vest (e.g., sensor belt 130, 200 or 310) and a data recorder (DR) (e.g., DR 120), and swallows an in-vivo device (e.g., device 110 or device 320).

At step 410, magnetic field interferences (MFIs), which are magnetic fields generated by sources other than the belt's magnetic coils, may initially be detected by a controller (e.g., controller 124, FIG. 1) using the sensor belt's magnetic field sensors (e.g., magnetic field sensors S1-Sm, FIG. 2). The controller may detect MFIs in order to compensate for the interfering signals induced by MFIs in the belt's magnetic field sensors, or in some of the belt's sensors, during the calibration process. The controller may detect MFIs, for example, a few seconds or a few milliseconds before the controller starts a (new) belt calibration process. Preferably, the time the controller detects MFIs and the time the controller starts a belt calibration process are as close as possible in order to improve accuracy of the belt calibration process, hence accuracy of the sensor belt's geometry, hence the coordinates system used as a reference frame. The controller may sense the interfering magnetic fields before the controller calculates a geometry of the belt, or after the controller calculates a geometry of the belt (and then modify the belt's geometry accordingly).

After (e.g., immediately after) the controller detects MFIs the controller may calibrate the sensor belt to characterize/detect the belt's geometry. (The belt's geometry defines a coordinate system that is used to localize the in-vivo device. That is, the belt's geometry may define a coordinate system relative to which the location of the device may be determined) As described, for example, above, the sensor belt calibration process (at step 410) may include a step or steps for filtering out interference signals that extraneous/interfering electromagnetic field sources may induce in the magnetic field sensors during a sensor belt's calibration process. For example, a sensor belt calibration process may include a step of measuring/reading interference signals that are induced in all or in some of the magnetic sensors by interfering magnetic field sources. During this step, the sensor belt's magnetic coils are muted/deactivated so that the magnetic field sensors are subjected only to interfering magnetic fields. The signals measured by the magnetic sensors, a signal per magnetic sensor, may be filtered out or compensated for (e.g., by a controller) during the rest of the belt's calibration process, to improve the localization accuracy.

At step 420, determine the location of a swallowed in-vivo device by using the sensor belt. If the location of the in-vivo device is to be determined again (the condition is shown as "No" at step 430), then, it is checked, at step 440, if another calibration of the belt is required or scheduled. (A controller may be configured to calculate a current geometry of the belt according to a predefined or dynamically changing schedule or time arrangement.) The condition whether another belt calibration is required may be checked per a predetermined criterion, which may be, for example, time-based, capsule movement based, capsule acceleration based, image frame capturing rate, etc.

If, per a predetermined criterion, it is determined (e.g., by a controller) at step 440 that another calibration is not required (the condition is shown as "No" at step 440), then localization of the in-vivo device may be determined at step 420 without recalibrating the belt (e.g., using the last calculated geometry of the belt). Loop 450 may repeat or reiterate until a new belt recalibration is required. However, if, per the predetermined criterion, it is determined (e.g., by the controller) at step 440 that another calibration is required (the condition is shown as "Yes" at step 440), then another belt calibration process may commence (460), at step 410, after which the location of the in-vivo device may be determined, at step 420, by using the updated, modified, or adjusted, belt geometry.

In other words, localizing an in-vivo device may include determining (e.g., calculating) a geometry of the sensor belt from magnetic fields generated by magnetic coils included or embedded in the sensor belt and sensed by magnetic field sensors included or embedded in the sensor belt, activating magnetic coils included or embedded in the sensor belt to generate magnetic fields, and determining a location of the in-vivo device, relative to the coordinate system, from magnetic fields sensed by magnetic field sensors included or embedded in the in-vivo device.

Figure 5:
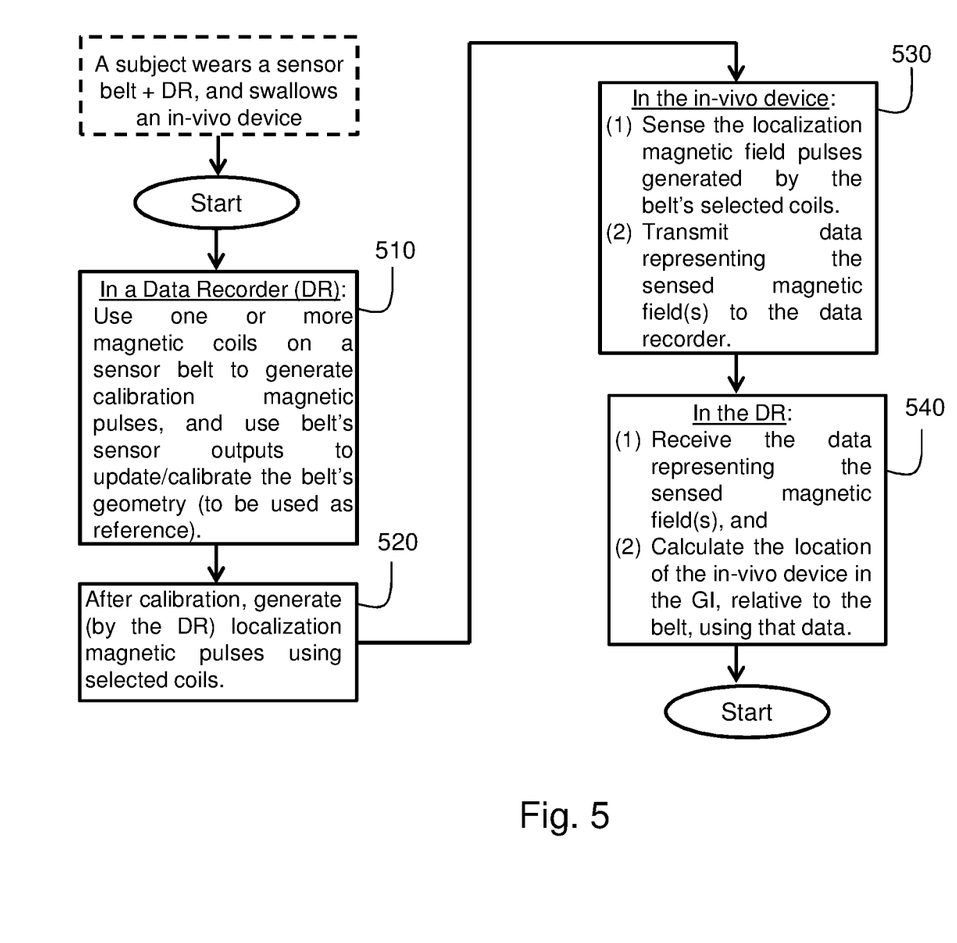
FIG. 5 shows a method for localizing an in-vivo device according to another example embodiment of the invention.

FIG. 5 shows a method for operating/using belt 200/310 according to another example embodiment of the invention. Steps described in connection with the method shown in FIG. 5, and with the other methods disclosed herein, may be performed by a controller, for example by a controller 124 of FIG. 1, or a similar controller. Assume that a subject wears a sensor belt (e.g., sensor belt 130, 200 or 310) and a data recorder (DR) (e.g., DR 120), and swallows an in-vivo device (e.g., device 110 or device 320).

At step 510, perform, in the DR, the steps: select and use one or more magnetic coils mounted on/in the sensor belt to generate magnetic field pulses, and select (and use the selected) sensor outputs to detect, or calculate, the belt's geometry in order for the belt's geometry to be used as a coordinate system (reference frame). The step(s) during which the one or more magnetic coils mounted on/in the sensor belt generate the magnetic field pulses may include a step, or be preceded by a step, of filtering out interference signals that extraneous/interfering electromagnetic field sources may induce in the sensor outputs during the belt's calibration process. At step 520, after the sensor belt's geometry is determined (e.g., detected or calculated), localization magnetic pulses may be generated (e.g., by the DR) using selected coils.

At step 530, perform, in the in-vivo device, the steps: (1) sense, using one or more magnetic field sensors (e.g., three 3-Dimensional magnetometers), the localization magnetic field pulses generated by the belt's selected coils, and (2) transmit, from/by the in-vivo device to the data recorder, data representing the magnetic characteristics/vector(s) (e.g., magnitude, direction) of or related to the sensed magnetic field(s).

At step 540, perform, in the DR, the steps: (1) receive, from the in-vivo device, the data representing the sensed magnetic field(s), and (2) calculate the location of the in-vivo device in the GI, relative to the sensor belt (e.g., using the belt's calculated geometry), using the received data representing the sensed magnetic field(s).

Figure 6:
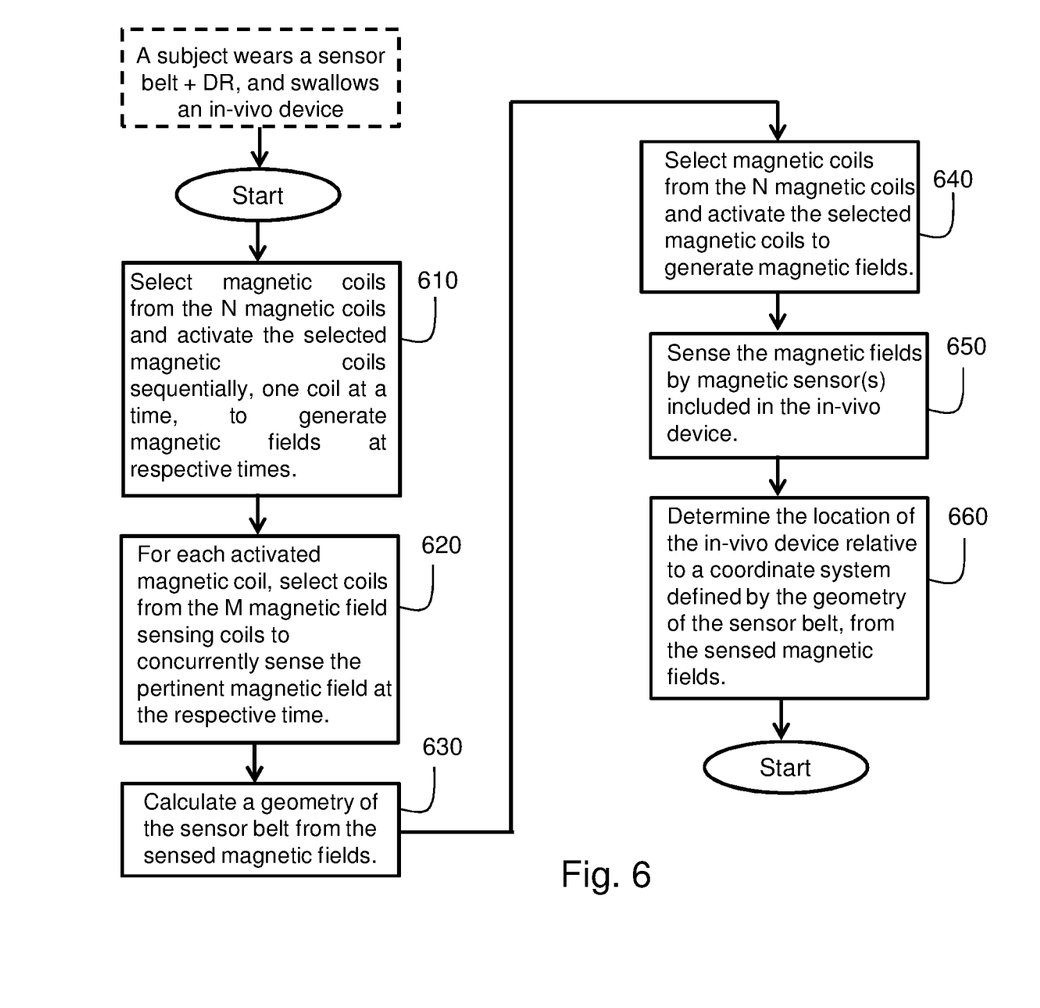
FIG. 6 shows a method for localizing an in-vivo device according to another example embodiment of the invention.

FIG. 6 shows a method for operating/using belt 200/310 according to another example embodiment of the invention. Steps described in connection with the method shown in FIG. 6 may be performed by a controller, for example by a controller 124 of FIG. 1, or by a similar controller. Assume that a subject wears a sensor belt (e.g., sensor belt 130, 200 or 310) and a data recorder (DR) (e.g., DR 120), and swallows an in-vivo device (e.g., device 110 or device 320).

At step 610, select magnetic coils from the N magnetic coils and activate the selected magnetic coils sequentially, e.g., one coil at a time, to generate magnetic fields at respective times (e.g., at different times, one coil being activated at each different time). For each activated magnetic coil, select, at step 620, coils from the M magnetic field sensors to concurrently sense the pertinent (respective) magnetic field at the respective time. At step 630, the geometry or shape of the sensor belt or garment may be calculated or determined from the sensed magnetic fields. In one embodiment, it is the positional arrangement of the coils and/or sensors in or on the belt or garment that is calculated or determined, and from this the geometry or shape of the belt or garment may be determined.

At step 640, select magnetic coils from the N magnetic coils and activate the selected magnetic coils to generate magnetic fields, and, at step 650, sense the magnetic fields by magnetic field sensor(s) which are included or embedded in the in-vivo device. At step 660, determine, from the sensed magnetic fields, the location of the in-vivo device relative to a coordinate system defined by the geometry of the sensor belt.

Figure 7:
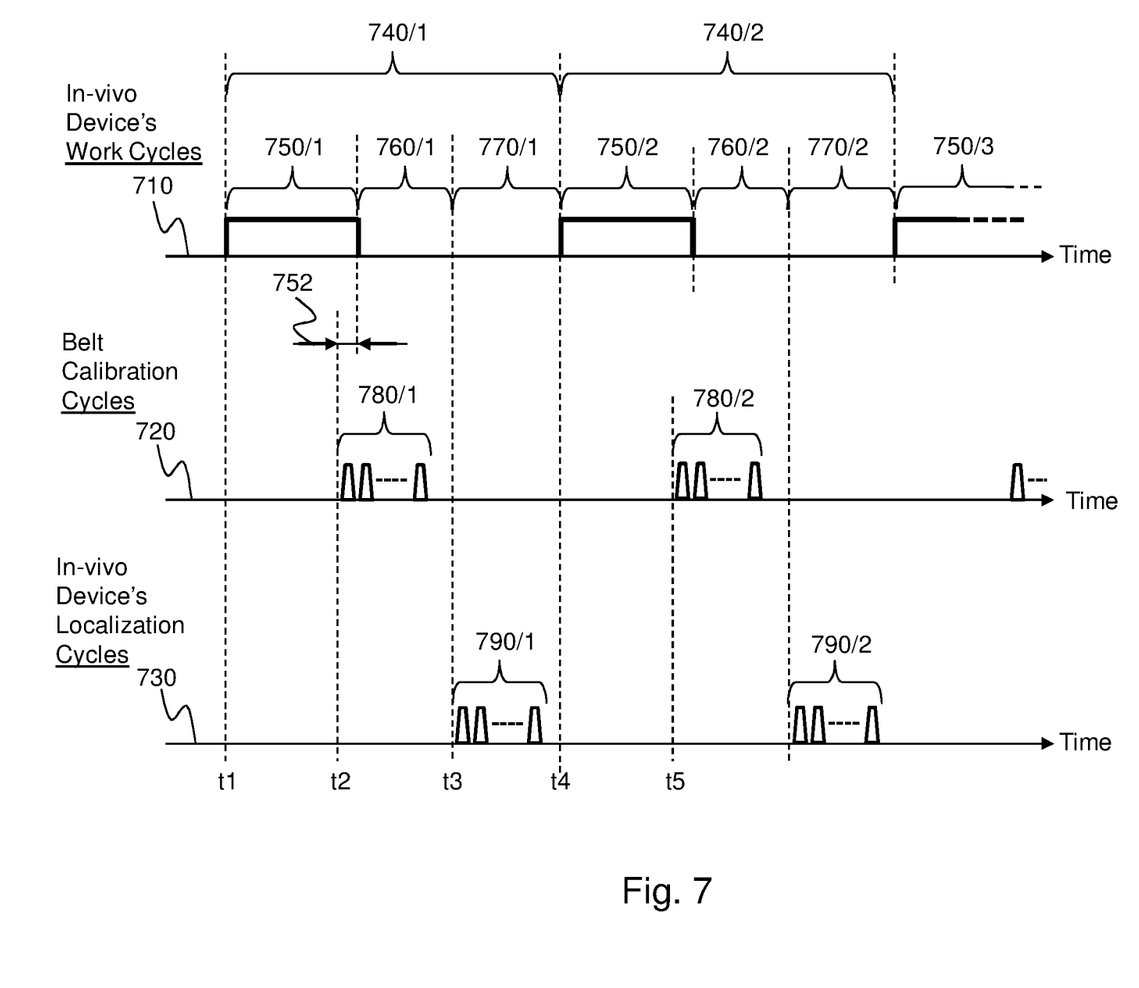
FIG. 7 shows a time diagram according to an example embodiment of the invention.

FIG. 7 is a timing diagram according to an example embodiment of the present invention. By way of example, the timing diagram includes three graphs, shown at 710, 720 and 730. By way of example, graph 710 shows two example work cycles 740/1 and 740/2 of an in-vivo device in accordance with the present invention.

The in-vivo device may include (but this is not mandatory) one or more sensors (e.g., pH sensor(s), pressure sensor(s), temperature sensor(s), imager(s), etc.) for sensing physiological parameters of, or for imaging, the GI tract traversed by the in-vivo device. Each work cycle 740 of the in-vivo device may include, be divided or segmented to, three or more apportioned time slots or time windows to accommodate for, for example, transmission of sensory data (e.g., to a data recorder) and for the calibration of the sensory belt and the localization process as described herein. For example, work cycle 740/1 may include three time slots/windows, which are designated as time slots/windows 750/1, 760/1 and 770/1, to respectively accommodate for, for example, transmission of sensory data from/by the in-vivo device, calibration of the sensory belt (which is a process taking place outside the in-vivo device) and localization process which is done using both the in-vivo device and a data recorder, or another external device.

Regarding work cycle 740/1, a first time slot/window (e.g., slot/window 750/1) may be used to wirelessly transmit sensory data (and optionally other type(s) of data) from the in-vivo device to an external data recorder. A second time slot/window (e.g., slot/window 760/1) may be pre-assigned to or pre-allocated for the belt's calibration process described herein. A time slot/window (e.g., slot/window 760/1), though pre-assigned or pre-allocated for the belt's calibration process, may be skipped in some work cycles, as the belt's calibration process may be performed once in a while, for example once every X (X=2, 3, . . . etc.) work cycles 740 (e.g., once every 3 work cycles 740). A third time slot/window (e.g., slot/window 770/1) may be pre-assigned or pre-allocated for sensing, by the in-vivo device, localization magnetic field pulses that are generated by coils mounted in/on a sensor belt).

Graph 720 shows two example calibration series (780/1 and 780/2) of magnetic field activations of the sensor belt. Each series of magnetic field activations may include K activations of magnetic coils of the sensor belt. During each activation of the sensor belt, the data recorder may select a particular magnetic coil, generate a magnetic field pulse using the selected coil and, simultaneously or concurrently, sense the magnetic field pulse using a particular set of coils that the data recorder selects. The data recorder may select a different magnetic coil for effecting each of the K (K=1, 2, . . . , etc.) activations, and it may select a different set of coils for each activation for sensing the pertinent magnetic field pulse. (A set of coils may include one coil.)

Since the in-vivo device may transmit sensory data to data recorder using RF transmission and the belt calibration process is implemented using magnetic field pulses, the two processes may be independent of one another. Therefore, the temporal location of calibration series 780/1 of magnetic field activations, relative to transmission time 750/1, may be as shown in FIG. 6 (e.g., there may be some overlapping, as shown at 752), or the calibration series 780/1 of magnetic field activations may completely reside in time slot/window 760/1. (The same principle may apply to calibration series 780/2 of magnetic field activations, and to every subsequent calibration series.)

Graph 730 shows two example localization series (790/1 and 790/2) of magnetic field activations of the sensor belt. Each series of magnetic field activations may include L activations of magnetic coils of the sensor belt. During each activation of the sensor belt, the data recorder may select a particular magnetic coil and generate a magnetic field pulse using the selected coil in order for the in-vivo device to concurrently sense the magnetic field pulse using the in-vivo device's own magnetic field sensor(s). The data recorder may select a different magnetic coil for each of the L (L=1, 2, . . . , etc.) activations. K may be the number of magnetic pulses required to enable accurate calculation of the belt's geometry. L may be the number of magnetic pulses required to enable accurate determination the location of the in-vivo device. Therefore, K and L may be selected using different constraints, though some constraints related to the belt's calibration process and some constraints related to the in-vivo device's localization process may be interrelated, or they may have to coexist. Example constraints may include, or be associated with, the time required by the in-vivo device to receive a localization magnetic field pulse and process it, the number of localization magnetic field pulses required to reliably determine a localization of the in-vivo device, the number of belt's coils and sensors required to reliably determine the belt's geometry and the time required by the data recorder to process sensor outputs in response to the generation of each magnetic field pulse by the belt's coils, and so on.

Each time a localization magnetic pulse (of series 790) is generated by the data recorder, it is sensed, for example during time slot/window 770, by one or more magnetic field sensors in the in-vivo device. The in-vivo device may process the output signals of the magnetic field sensors and generate a corresponding data that represents the magnetic characteristics of the magnetic pulses as sensed by the in-vivo device's sensors. The in-vivo device may transmit the corresponding data to the data recorder, for example, during a subsequent in-vivo device's transmission time slot/window 750, for example during time slot/window 750/2.

The controller mentioned herein may be configured to use the M magnetic field sensors to sense interfering magnetic fields which are not generated by the N magnetic coils, and to sense the interfering magnetic fields before the controller calculates a geometry of the belt, or thereafter. The controller may be configured to filter out the interfering magnetic fields when calculating a current geometry of the belt. The controller may be configured to adjust a calculated geometry of the belt according to the sensed interfering magnetic fields. The controller may be configured to calculate a geometry of the belt based on the magnetic fields originating from the magnetic coils and also based on the interfering magnetic fields. (The interfering magnetic fields may include magnetic field(s) originating from external source(s), for example an interfering magnetic field may be the earth's magnetic field.)

During localization of an in-vivo device, the current location of the in-vivo device is known (e.g., to a controller). 'Knowing' the current device's location and past locations enables, for example the controller, to anticipate, or to 'guess', the next location of the device. Anticipating the device's next location may be beneficial in terms of selection of the magnetic coils used to locate the in-vivo device. As described above, the magnetic characteristics of the magnetic field, in particular the magnetic gradient (e.g., AB/AX), that is generated by each magnetic coil are known. (Small magnetic gradient means that the magnetic field changes relatively slowly with distance, and, in such cases, the location determination process is less accurate, and vice versa.)

Since each of the N magnetic coils has/causes a known magnetic gradient at the anticipated location of the in-vivo device, at least three coils having the maximal 'minimal gradients' can be selected for localizing the in-vivo device. This coil selection method may ensure that the localization process is performed with high accuracy, given the anticipated location of the device and the current geometry of the sensor belt.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to". For example, assume that Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory or a USB flash memory storing instructions, e.g., computer-executable instructions, which, when executed by a processor or controller, carry out methods disclosed herein. Some embodiments may be provided in a computer program product that may include a non-transitory machine-readable medium, having stored thereon instructions, which may be used to program a computer, or other programmable devices, to perform methods as disclosed above.

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant, for example, to various types of in-vivo devices and to various types of magnetic generating systems and magnetic field sensors. Hence the scope of the claims that follow is not limited by the disclosure herein.

The invention claimed is:

1. A sensor belt system for localizing an in-vivo device in a gastrointestinal tract of a subject, comprising:
   a belt wearable by a subject;
   a number N of magnetic coils distributed in the belt, to generate magnetic fields;
   a number M of magnetic field sensors distributed along the length of the belt, to sense magnetic fields; and
   a controller configured to:
   select magnetic coils from the N magnetic coils and activate the selected magnetic coils sequentially to generate magnetic fields;
   select, for each activated magnetic coil, magnetic field sensors from the M magnetic field sensors to sense a generated magnetic field; and
   calculate a geometry of the belt from the sensed magnetic fields, said geometry to be used as a coordinate system for localizing an in-vivo device.

2. The sensor belt system as in claim 1, wherein the N magnetic coils are interspersed between the M magnetic field sensors coils.

3. The sensor belt system as in claim 1, wherein the controller is configured to calculate a current geometry of the belt according to a schedule.

4. The sensor belt system as in claim 3, wherein the belt's geometry calculation schedule is predefined.

5. The sensor belt system as in claim 1, wherein a belt geometry calculation is performed according to a criteria.

6. The sensor belt system as in claim 5, wherein a criterion is selected based on past geometries of the belt.

7. The sensor belt system as in claim 1, wherein the controller is configured to use the M magnetic field sensors to sense interfering magnetic fields which are not generated by the N magnetic coils.

8. The sensor belt system as in claim 7, wherein the controller is configured to sense the interfering magnetic fields before the controller calculates a geometry of the belt.

9. The sensor belt system as in claim 7, wherein the controller is configured to factor in the interfering magnetic fields when calculating a current geometry of the belt.

10. The sensor belt system as in claim 7, wherein the controller is configured to adjust a calculated geometry of the belt according to the sensed interfering magnetic fields.

11. The sensor belt system as in claim 7, wherein the controller is configured to calculate a geometry of the belt based on the magnetic fields originating from the magnetic coils and also based on the interfering magnetic fields.

12. The sensor belt system as in claim 7, wherein the interfering magnetic fields comprise magnetic field(s) originating from external source(s).

13. The sensor belt system as in claim 7, wherein the interfering magnetic fields comprise the earth's Earth's magnetic field.

14. The sensor belt system as in claim 1, wherein the controller is embedded in the belt.

15. The sensor belt system as in claim 1, further comprising a receiver electrically connectable to the belt.

16. The sensor belt system as in claim 15, wherein the controller is embedded in the receiver and electrically connected to the N magnetic field coils and to the M magnetic field sensors.

17. The sensor belt system as in claim 1, wherein the controller is configured to generate magnetic fields by selectively activating magnetic field coils, one coil at a time, in order for the magnetic fields to be sensed by magnetic field sensors included in an in-vivo device swallowed by a subject, and wherein the controller is further configured to receive, from the in-vivo device, data representing magnetic characteristics of the magnetic fields as sensed by the magnetic field sensors included in the in-vivo device.

18. The sensor belt system as in claim 17, wherein the controller is configured to detect the location of the in-vivo device in the subject based on data the controller receives from the in-vivo device in response to the magnetic fields the controller generates.

19. The sensor belt system as in claim 18, wherein the controller is configured to use a magnetic coil included in the belt as an origin point of a coordinate system relative to which the location of the in-vivo device is to be calculated.

20. The sensor belt system as in claim 18, wherein the controller is configured to optimize selection of the magnetic coils used to localize the in-vivo device.

21. The sensor belt system as in claim 20, wherein an optimization process comprises selecting magnetic coils that result in minimum electrical power.

22. A method for localizing an in-vivo device swallowed by a subject, comprising:

for a sensor belt worn by the subject and including N magnetic coils and M magnetic field sensors performing, selecting magnetic coils from the N magnetic coils and activating the selected magnetic coils sequentially to generate magnetic fields;

for each activated magnetic coil, selecting magnetic field sensors from the M magnetic field sensors to concurrently sense a generated magnetic field;

calculating a geometry of the sensor belt from the sensed magnetic fields, said geometry defining a coordinate system;

selecting magnetic coils from the N magnetic coils and activating the selected magnetic coils to generate magnetic fields;

sensing the magnetic fields by magnetic field sensor(s) included in the in-vivo device; and determining the location of the in-vivo device relative to the coordinate system from the sensed magnetic fields.

23. A method for localizing an in-vivo device swallowed by a subject, comprising:

for a sensor belt worn by the subject and including N magnetic coils and M magnetic field sensors performing, calculating a geometry of the sensor belt from magnetic fields generated by magnetic coils included in the sensor belt and sensed by magnetic field sensors included in the sensor belt, the sensor belt geometry defining a coordinate system;

activating magnetic coils included in the sensor belt to generate magnetic fields; and determining a location of the in-vivo device, relative to the coordinate system, from magnetic fields sensed by magnetic field sensors included in the in-vivo device.

* * * * *